United States Patent
Padinger et al.

(10) Patent No.: US 8,454,894 B2
(45) Date of Patent: Jun. 4, 2013

(54) DEVICE FOR EVALUATING BIOCHEMICAL SAMPLES

(75) Inventors: Franz Padinger, St. Marien (AT); Klaus G. Schröter, Berlin (DE)

(73) Assignee: ASMAG-Holding GmbH, Gruenau im Almtal (AT)

( * ) Notice: Subject to any disclaimer, the term of this patent is extended or adjusted under 35 U.S.C. 154(b) by 482 days.

(21) Appl. No.: 11/662,321

(22) PCT Filed: Aug. 24, 2005

(86) PCT No.: PCT/AT2005/000338
§ 371 (c)(1),
(2), (4) Date: Mar. 26, 2007

(87) PCT Pub. No.: WO2006/026796
PCT Pub. Date: Mar. 16, 2006

(65) Prior Publication Data
US 2007/0292307 A1   Dec. 20, 2007

(30) Foreign Application Priority Data
Sep. 8, 2004  (AT) ................... A 1502/2004

(51) Int. Cl.
*G01N 27/00* (2006.01)
(52) U.S. Cl.
USPC ..... 422/82.01; 422/501; 422/68.1; 422/82.08
(58) Field of Classification Search
None
See application file for complete search history.

(56) References Cited

U.S. PATENT DOCUMENTS

| | | | | |
|---|---|---|---|---|
| 5,247,190 A | * | 9/1993 | Friend et al. | 257/40 |
| 5,504,323 A | * | 4/1996 | Heeger et al. | 250/214.1 |
| 5,629,533 A | | 5/1997 | Ackley et al. | |
| 6,191,764 B1 | * | 2/2001 | Kono et al. | 345/76 |
| 6,303,943 B1 | * | 10/2001 | Yu et al. | 257/40 |
| 6,331,438 B1 | * | 12/2001 | Aylott et al. | 436/172 |
| 7,196,834 B2 | * | 3/2007 | Brabec et al. | 359/245 |
| 2004/0027462 A1 | | 2/2004 | Hing | |

FOREIGN PATENT DOCUMENTS

| | | |
|---|---|---|
| DE | 101 46 901 A1 | 9/2002 |
| DE | 101 46 902 A1 | 9/2002 |
| JP | 02 098177 A | 4/1990 |
| WO | WO 99/39395 A | 8/1999 |
| WO | WO03/015189 A1 * | 2/2003 |

OTHER PUBLICATIONS

International Search Report.
Yu G et al: "Semiconducting Polymer Diodes: Large Size, Low Cost Photodetectors With Excellent Visible-Ultraviolet Sensitivity" Applied Physics Letters, AIP, American Institute of Physics, Melville, NY, US, vol. 64, No. 25, Jun. 20, 1994, pp. 3422-3424, XP000454599, ISSN: 0003-6951 p. 3422; figure 1.

* cited by examiner

*Primary Examiner* — Sally Merkling
(74) *Attorney, Agent, or Firm* — Collard & Roe, P.C.

(57) ABSTRACT

Described is a device for evaluating biochemical samples (1), with a sample carrier (2), with an image recording means having a light-sensitive layer (3) connected to an evaluation circuit (10), and with a means for illuminating the samples (1). In order to provide simple design conditions, it is proposed that the light-sensitive layer (3), provided on the sample carrier (2), of the image recording means comprise a photoactive layer (4) based on organic semiconductors between two electrode layers (5, 6), of which the electrode layer (6) between the photoactive layer (4) and the samples (1) is translucent at least in certain regions.

10 Claims, 3 Drawing Sheets

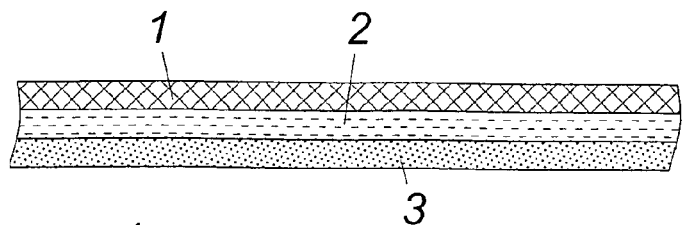
FIG.1
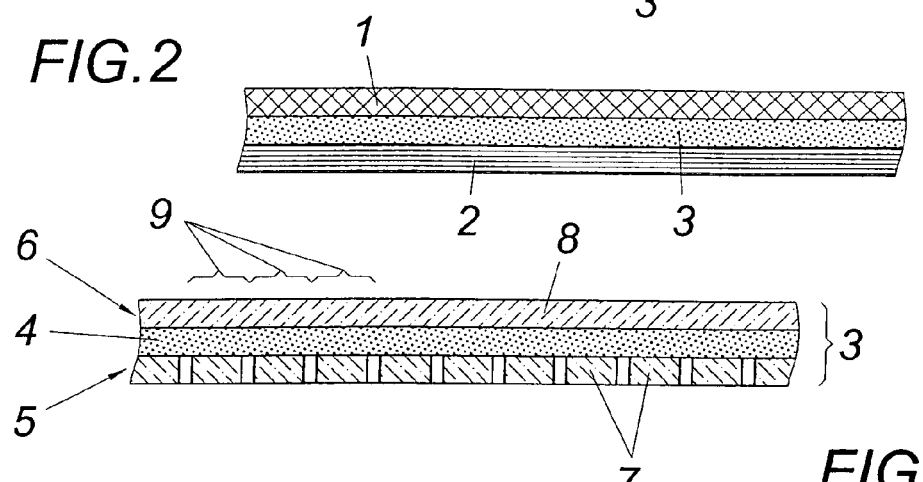
FIG.2
FIG.3
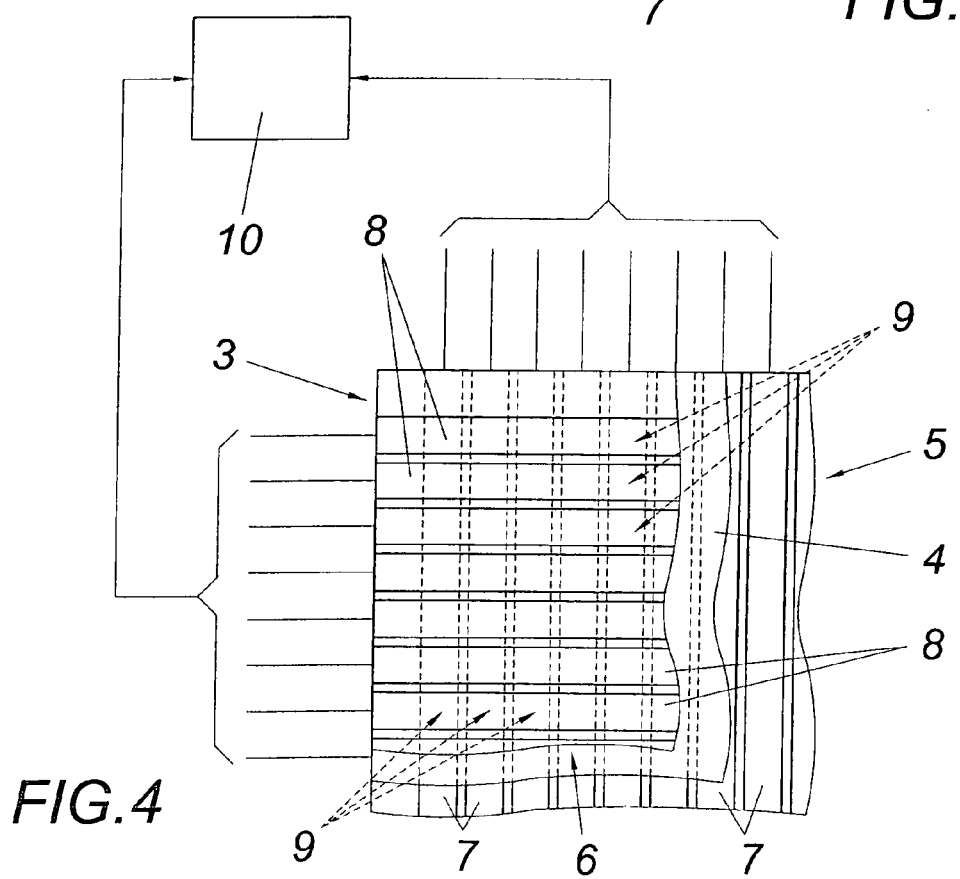
FIG.4

FIG.7

DEVICE FOR EVALUATING BIOCHEMICAL SAMPLES

CROSS REFERENCE TO RELATED APPLICATIONS

Applicants claim priority under 35 U.S.C. §119 of Austrian Application No. A 1502/2004 filed Sep. 8, 2004. Applicants also claim priority under 35 U.S.C. §365 of PCT/AT2005/000338 filed Aug. 24, 2005. The international application under PCT article 21(2) was not published in English.

1. Field of the Invention

The invention relates to a device for evaluating biochemical samples, with a sample carrier, with an image recording means having a light-sensitive layer connected to an evaluation circuit, and with a means for illuminating the samples.

2. Description of the Prior Art

The fact that in specific reactions between a biomolecular layer and a reagent a spectral change, discernible as a colour change, in the absorption of light occurs within the biomolecular layer or excitation with light causes correspondingly labelled biomolecules to emit, for example, fluorescent radiation can be used to investigate using an image recording means samples of this type with regard to a spectral change in absorption behaviour or the emission of fluorescent radiation. For this purpose, it is known (DE 101 46 902 A1) to provide the image recording means with a layer of light-sensitive elements in a matrix arrangement corresponding to the arrangement of the samples on the carrier, so the light received from the illuminated samples via an optical lens system of the individual light-sensitive elements can be allocated to the individual samples and evaluated. The light-sensitive elements used in thin-layer technology are photodiodes or phototransistors which can be read out individually into an evaluation circuit. The main drawback of this known device for evaluating biochemical samples is the cost which is associated with the image recording means and relates not only to the structural design of the image recording means but also to the optical lens system between the sample carrier and the image recording means, and also to the precise orientation of the sample carrier with respect to the lens system or the image recording means.

SUMMARY OF THE INVENTION

The object of the invention is accordingly to construct a device for evaluating biochemical samples of the type described at the outset in such a way that simple constructional means can ensure reliable evaluation of the samples.

The invention achieves the object set in that the light-sensitive layer, provided on the sample carrier, of the image recording means comprises a photoactive layer based on organic semiconductors between two electrode layers, of which the electrode layer between the photoactive layer and the samples is translucent at least in certain regions.

The use of a photoactive layer based on organic semiconductors results in comparatively simple design conditions based on the solubility of the organic semiconductor materials in conventional solutions. This means that an image recording means based on organic semiconductors can be attached to the carrier for the biochemical samples inexpensively compared to photodiodes or phototransistors based on inorganic semiconductors, and this allows direct allocation of the light-sensitive layer to the samples, so an optical lens system can advantageously be dispensed with. This applies not only to the recording of individual samples but also to the evaluation of a large number of samples which are attached to a carrier and to which light-sensitive elements have to be assigned in a matrix order corresponding to the order of samples.

That is to say, owing to the low movability, compared to inorganic semiconductors, of the charge carriers of photoactive layers based on organic semiconductors, no special measures are required to delimit individual light-sensitive regions from one another. For this purpose, the two electrode layers for the photoactive layer have merely to be constructed from intersecting strip conductors; which delimit, in the region of intersection, light-sensitive elements in the photoactive layer because, on account of the comparatively low charge movability, the conveyance of charge is restricted substantially to the region of intersection of the strip conductors and the influence of charge movement between adjacent regions of intersection of the strip conductors within the photoactive layer can generally be disregarded.

The light-sensitive layer can, in this case, be provided on the side of the sample carrier that is remote from the samples or between the sample carrier and the samples. In both possible embodiments, the light issuing from the samples can be detected directly via the photoactive layer, without an optical lens system. However, the photoactive layer on the side of the sample carrier that is remote from the samples requires the sample carrier to be translucent at least in certain regions.

If the spectral change, caused by a reaction of the samples with a reagent, in the absorption of light is observed, the samples can be illuminated from the side remote from the photoactive layer in order to detect the transmitted light and hence the absorption of light. However, such external illumination of the samples is not necessary if a reflection of light on the samples is used for this purpose. The same applies to the evaluation of radiation, for example fluorescent radiation, excited by light. In these cases, the light required for reflection or the light required for exciting the radiation of the correspondingly labelled biomolecules can be sent from a light-emitting layer on the side, remote from the samples, of the light-sensitive layer which is therefore to be translucent; this does not present any difficulties to the photoactive layer with regard to the use of organic semiconductors. The provision of a light-emitting layer on the side of the light-sensitive layer that is remote from the samples renders the device independent of external illumination conditions, and this broadens the range of possible uses and ensures simple handling.

The light-emitting layer can be constructed from electroluminescent diodes using thin-layer technology. However, particularly advantageous design conditions are obtained if the light-emitting layer has a photoactive layer based on organic semiconductors between two electrode layers, of which the electrode layer between the photoactive layer and the light-sensitive layer is translucent at least in certain regions. For the light-emitting layer, advantages with regard to construction and activation similar to those in the layer of light-sensitive elements can thus be utilised, especially if the two electrode layers for the photoactive layer of the light-emitting layer have intersecting strip conductors delimiting, in the region of intersection, light-emitting elements in the photoactive layer.

If a respective photoactive layer is used for the light-sensitive and the light-emitting layer, the electrode layers can be separated from one another by an insulating layer on the mutually facing sides of the two photoactive layers. However, it is also possible to provide for the photoactive layer of the light-sensitive layer and the photoactive layer of the light-emitting layer a common electrode layer between the two layers, and this simplifies the design.

As photoactive layers based on organic semiconductors can be used as both the light-sensitive and the light-emitting layer, there is no need for a separate light-emitting layer if an electrical voltage is applied to selected regions of the photoactive layer via the associated strip conductors of the two electrode layers for light emission. Via these light-emitting regions, the samples to be examined can be acted on by light in order to be able to detect either the light reflected by the samples or radiation excited by the emitted light through light-sensitive regions adjacent to the light-emitting regions.

The demands, on the one hand, for high light sensitivity and, on the other hand, for an effective light yield with low excitation energy necessitate generally differing measures with regard to the construction of the photoactive layer. For this reason, the photoactive layer can have, in the region of the light-emitting elements, a construction differing from the regions of the light-sensitive elements. Two molecular components can thus be used for the light-sensitive regions of the photoactive layer, namely a conjugated polymer component as the electron donor and a fullerene component as the electron acceptor, whereas merely a conjugated polymer is used for the light-emitting elements. The absence of an electron acceptor allows light to be emitted on application of an electrical voltage to these polymer regions.

The output signals from the light-sensitive elements can be read out into the evaluation circuit as a function of the local position of the respectively activated light-emitting elements. In this case, it is possible to evaluate the samples individually or in groups as a function of the activation of the light-emitting elements, and this restricts the excitation energy to be provided for the light-emitting elements which, after all, can be successively activated in any desired sequence. In addition, the output signals from the light-sensitive elements can also be carried out as a function with respect to time of the activation of the light-emitting elements. This measure can ensure that the emitted light for exciting fluorescent radiation does not impair the measurement of the fluorescent radiation.

BRIEF DESCRIPTION OF THE DRAWINGS

The drawings show the subject-matter of the invention by way of example. In the drawings:

FIG. 1 is a simplified cross section of a device according to the invention for evaluating biochemical samples, FIG. 2 is a view, corresponding to FIG. 1, of a design variation of a device according to the invention, FIG. 3 is a cross section of the basic construction of a layer of light-sensitive elements, FIG. 4 is a partially exploded plan view of the layer of light-sensitive elements shown in FIG. 3, FIGS. 6 and 7 show modified embodiments of devices corresponding to FIG. 5.

DESCRIPTION OF THE PREFERRED EMBODIMENT

Figure 5:
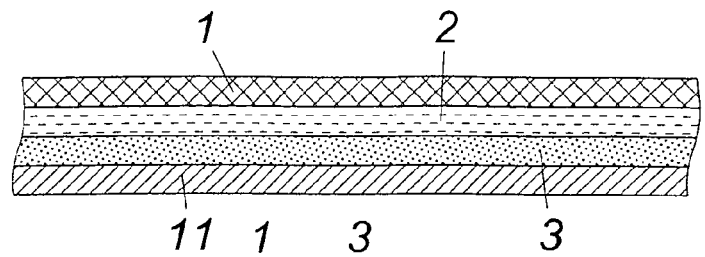
FIG. 5 is a schematic cross section of a further embodiment of a device according to the invention having, in addition to a layer of light-sensitive elements, a layer of light-emitting elements.

As shown in FIG. 1, the biochemical samples 1 to be evaluated are attached to a translucent sample carrier 2, either in the form of a continuous layer or in mutually separated regions. On the side of the translucent sample carrier 2 that is remote from the samples 1, there is provided a light-sensitive layer 3 allowing the spectral change, occurring in the event of a corresponding reaction of the samples with a reagent, in the absorption of light radiation to be determined by the detection of the transmitted light or fluorescent radiation, excited using light, of correspondingly labelled biomolecules. As may be seen from FIG. 2, the light-sensitive layer 3 can also be arranged between the samples 1 and the sample carrier 2, so the samples 1 are attached to the light-sensitive layer 3, an insulating layer optionally being interposed. In this case, the sample carrier 2 does not have to be translucent.

The light-sensitive layer 3 has, as shown in FIGS. 3 and 4, a photoactive layer 4 between two adjoining electrode layers 5, 6 consisting of intersecting strip conductors 7, 8. The photoactive layer 4 is constructed on the basis of organic semiconductors, the charge movability of which parallel to the layer face is comparatively small, thus producing in the region of intersection of the strip conductors 7, 8 light-sensitive elements 9 substantially separated from one another. Although the construction of the photoactive layer 4 can differ, particularly beneficial conditions with regard to the formation of the light-sensitive elements are obtained if the photoactive layer 4 is composed of two molecular organic components, namely of a conjugated polymer component as the electron donor and a fullerene component as the electron acceptor. The light-sensitive elements 9 are connected to an evaluation circuit 10 via the strip conductors 7, 8, as indicated in the manner of a block diagram in FIG. 4. The output signals from the light-sensitive elements 9 of the layer 3 can thus be read out into the evaluation circuit 10 in any desired order for evaluating the samples 1. As the light radiation received from the samples 1 has to penetrate the electrode layer 6 between the samples 1 and the photoactive layer 4, this electrode layer 6 must be translucent at least in certain regions.

Figure 6:
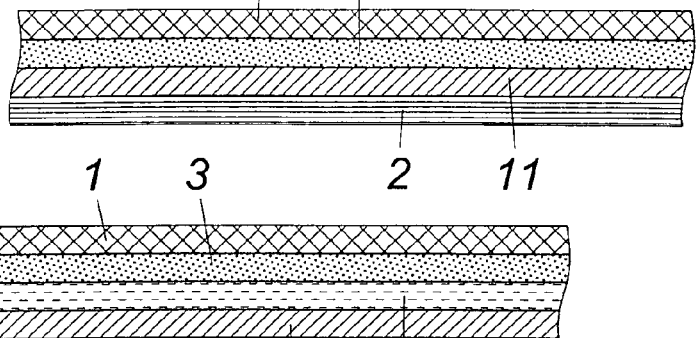

The samples 1 can be illuminated externally, i.e. from the side of the samples 1 that is remote from the light-sensitive layer 3. However, more beneficial design conditions are obtained if a light-emitting layer 11 associated with the sample carrier 2 is provided for illuminating the samples 1, as is shown in FIGS. 5, 6 and 7. The device shown in FIG. 5, which starts from an arrangement of the light-sensitive layer 3 as shown in FIG. 1, forms the light-emitting layer 11 on the side of the light-sensitive layer 3 that is remote from the sample carrier 2. This means that not only the photoactive layer 4 but also the adjoining electrode layers 5 and 6 have to be translucent at least in certain regions. The devices shown in FIGS. 6 and 7 start from an arrangement of the light-sensitive layer 3 corresponding to FIG. 2, the light-emitting layer 11 being provided, as shown in FIG. 6, between the sample carrier 2 and the light-sensitive layer 3. In contrast thereto, the light-emitting layer 11 as shown in FIG. 7 is displaced onto the side, remote from the light-sensitive layer 3, of the sample carrier 2 which in this case has to be translucent at least in certain regions.

Figure 8:
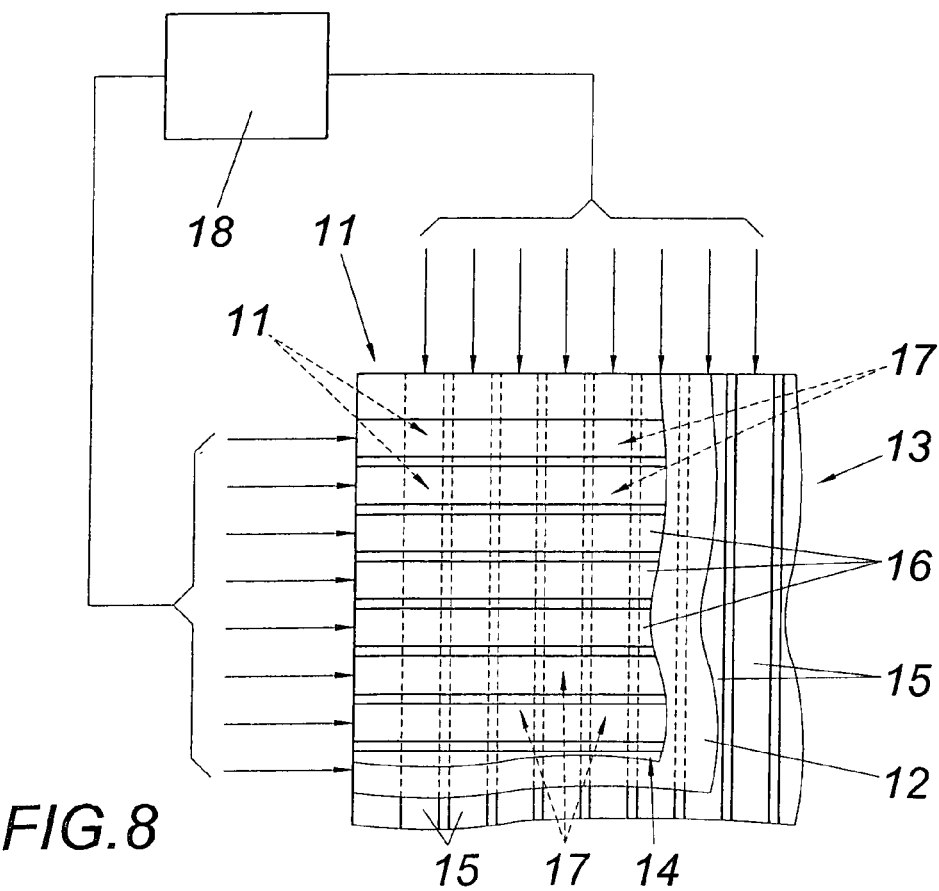
FIG. 8 is a partially exploded plan view of a layer of light-emitting elements.

The light-emitting layer 11, like the light-sensitive layer 3, can advantageously have a photoactive layer 12 based on organic semiconductors between two electrode layers 13 and 14, as is indicated in FIG. 8. These electrode layers 13 and 14 can, in turn, comprise intersecting strip conductors 15, 16, in the region of intersection of which the light-emitting elements 17, which can be activated individually, are produced. An electrical voltage can be applied to the individual strip conductors 15 and 16 via a control means 18 to excite the respectively activated elements 17 to emit light radiation which penetrates the photoactive layer 4 of the layer 3 of light-sensitive elements and optionally the sample carrier 2, so the samples 1, when labelled accordingly, are excited to emit radiation which, in turn, is detected by the light-sensitive elements 9 of the layer 3 and evaluated in the evaluation circuit 10. For reading out the output signals from the light-sensitive elements 9, both dependency with respect to location and dependency with respect to time of the activation of the light-emitting elements 17 can be utilised to avoid a measurement which takes account both of the light received from the samples 1 and the basic loading, caused by the emitted light from the layer 11, of the light-sensitive elements, although such a measurement is also possible.

Figure 9:
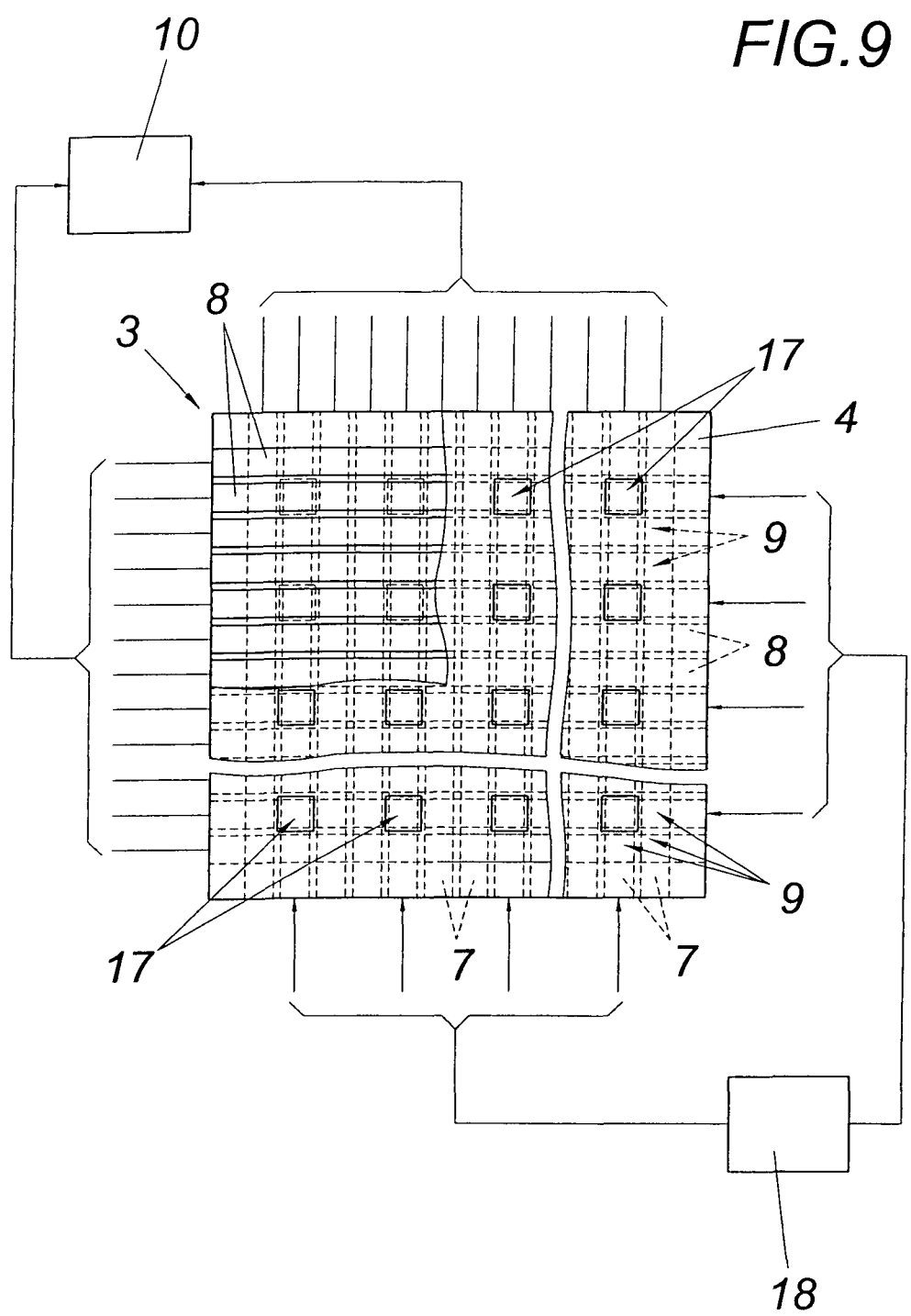
FIG. 9 is a partially exploded plan view of a photoactive layer forming both light-sensitive and light-emitting elements.

The construction of a photoactive layer based on organic semiconductors allows the regions, resulting in the region of intersection of strip conductors, of a photoactive layer of this type to serve, depending on the force acting on them, both as light-emitting and as light-sensitive elements. There is therefore no need to provide a separate layer 11 of light-emitting elements if the photoactive layer 4 forms light-emitting elements 17 in predetermined regions of intersection of the strip conductors 7 and 8. FIG. 9 indicates a layer 3 of this type with additional light-emitting elements 17. For this purpose, the photoactive layer 4 for the light-sensitive elements 9 and the light-emitting elements 17 can have a differing construction. In the local region of the light-emitting elements 17, the photoactive layer 4 preferably consists merely of a conjugated polymer, whereas the photoactive layer in the remaining region is composed of two molecular organic components, namely a conjugated polymer component as the electron donor and a fullerene component as the electron acceptor. FIG. 9 indicates these differing regions for the elements 9 and 17, the light-sensitive elements 9 being connected to the evaluation circuit 10 via the strip conductors 7, 8, whereas the light-emitting elements 17 are activated via a control means 18 connected to the strip conductors 7, 8 which intersect in the region of the light-emitting elements 17.

The invention claimed is:

1. A device for evaluating biochemical samples, the device comprising a sample carrier an image recorder comprising a light-sensitive layer connected to an evaluation circuit, wherein the light-sensitive layer, provided on the sample carrier of the image recorder comprises a photoactive layer based on organic semiconductors between two electrode layers of which the electrode layer between the photoactive layer and the samples is translucent at least in certain regions;
   wherein the two electrode layers for the photoactive layer are constructed from intersecting strip conductors which delimit, in the region of intersection, light-sensitive elements in the photoactive layer;
   wherein the photoactive layer forms light-emitting elements in selected regions of intersection of the strip conductors of the two electrode layers, the light-emitting elements in the photoactive layer being adjacent to but separate from the light-sensitive elements in the photoactive layer;
   wherein the photoactive layer has a construction in the region of the light-emitting elements differing from a construction in the regions of the light-sensitive elements;
   wherein the evaluation circuit is configured to read out output signals from the light-sensitive elements; and
   wherein the photoactive layer simultaneously:
      emits light via the light-emitting elements, and
      senses light via the light-sensitive elements such that the light-sensitive elements generate the output signals and such that the evaluation circuit reads out the output signals.

2. The device according to claim 1, wherein the light-sensitive layer is provided on the side, remote from the samples, of the sample carrier which is translucent at least in certain regions.

3. The device according to claim 1, wherein the light-sensitive layer is provided between the sample carrier and the samples.

4. The device according to claim 1, further comprising a further light-emitting layer on the side, remote from the samples, of the light-sensitive layer which is translucent at least in certain regions.

5. The device according to claim 4, wherein the further light-emitting layer has a photoactive layer based on an organic semiconductor between two electrode layers, of which the electrode layer between the photoactive layer and the light-sensitive layer is translucent at least in certain regions.

6. The device according to claim 5, wherein the two electrode layers for the photoactive layer of the further light emitting layer have intersecting strip conductors delimiting, in the region of intersection, light-emitting elements in the photoactive layer.

7. The device according to claim 1, wherein the photoactive layer of the light-sensitive layer and the photoactive layer of the further light-emitting layer have between them a common electrode layer.

8. The device according to claim 1, wherein the output signals from the light-sensitive elements are read out into the evaluation circuit as a function of the local position of the respectively activated light-emitting elements.

9. The device according to claim 1, wherein the output signals from the light-sensitive elements are read out into the evaluation circuit as a function with respect to time of the activation of the light-emitting elements.

10. A combination comprising:
   a biochemical sample on a sample carrier of a device for evaluating biochemical samples, the device comprising the sample carrier and an image recorder comprising a light-sensitive layer connected to an evaluation circuit, wherein the light-sensitive layer, provided on the sample carrier, of the image recorder comprises a photoactive layer based on organic semiconductors between two electrode layers, of which the electrode layer between the photoactive layer and the samples is translucent at least in certain regions;
   wherein the two electrode layers for the photoactive layer are constructed from intersecting strip conductors which delimit, in the region of intersection, light-sensitive elements in the photoactive layer;
   wherein the photoactive layer forms light-emitting elements in selected regions of intersection of the strip conductors of the two electrode layers, the light-emitting elements in the photoactive layer being adjacent to but separate from the light-sensitive elements in the photoactive layer;
   wherein the photoactive layer has a construction in the region of the light-emitting elements differing from a construction in the regions of the light-sensitive elements;
   wherein the evaluation circuit is configured to read out output signals from the light-sensitive elements; and
   wherein the photoactive layer simultaneously:
      emits light via the light-emitting elements, and
      senses light via the light-sensitive elements such that the light-sensitive elements generate the output signals and such that the evaluation circuit reads out the output signals.

* * * * *

UNITED STATES PATENT AND TRADEMARK OFFICE
CERTIFICATE OF CORRECTION

PATENT NO. : 8,454,894 B2  
APPLICATION NO. : 11/662321  
DATED : June 4, 2013  
INVENTOR(S) : Padinger et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 616 days.

Signed and Sealed this
Eighth Day of September, 2015

Michelle K. Lee
*Director of the United States Patent and Trademark Office*